(12) United States Patent
Hancock-Cooke et al.

(10) Patent No.: US 8,257,333 B2
(45) Date of Patent: Sep. 4, 2012

(54) ABSORBENT ARTICLE WITH AN ELASTIC WAISTBAND HAVING A PREFERRED RATIO OF ELASTIC TO NON-ELASTIC MATERIALS

(75) Inventors: Catherine M. Hancock-Cooke, Neenah, WI (US); Mark G. Everson, Neenah, WI (US); Paul J. Datta, Appleton, WI (US); John E. Kerins, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 838 days.

(21) Appl. No.: 10/324,666

(22) Filed: Dec. 20, 2002

(65) Prior Publication Data

US 2004/0122400 A1 Jun. 24, 2004

(51) Int. Cl.
*A61F 13/15* (2006.01)
*A61F 13/20* (2006.01)

(52) U.S. Cl. .............. 604/385.27; 604/385.22; 604/386

(58) Field of Classification Search ............. 604/385.01, 604/385.22, 385.24–385.27, 386
See application file for complete search history.

(56) References Cited

U.S. PATENT DOCUMENTS

| | | |
|---|---|---|
| 4,205,679 A | 6/1980 | Repke et al. |
| 4,639,949 A | 2/1987 | Ales et al. |
| 4,720,415 A | 1/1988 | Vander Wielen et al. |
| 4,808,176 A | 2/1989 | Kielpikowski |
| 4,857,067 A | 8/1989 | Wood et al. |
| 4,904,251 A | 2/1990 | Igaue et al. |
| 4,936,840 A | 6/1990 | Proxmire |
| 5,242,436 A | 9/1993 | Weil et al. |
| 5,569,234 A | 10/1996 | Buell et al. |
| 5,601,547 A | 2/1997 | Kato et al. |
| 5,676,661 A | 10/1997 | Faulks et al. |
| 5,683,376 A | 11/1997 | Kato et al. |
| 5,711,832 A | 1/1998 | Glaug et al. |
| 5,846,232 A * | 12/1998 | Serbiak et al. ........... 604/385.29 |
| 6,336,921 B1 | 1/2002 | Kato et al. |
| 6,358,350 B1 | 3/2002 | Glaug et al. |
| 6,488,202 B1 | 12/2002 | Seitz et al. |
| 6,617,016 B2 * | 9/2003 | Zhang et al. ................ 428/318.6 |

FOREIGN PATENT DOCUMENTS

| | | |
|---|---|---|
| WO | 9960972 | 12/1999 |
| WO | 0187588 A2 | 11/2001 |

OTHER PUBLICATIONS

U.S. Appl. No. 09/563,417, filed May 3, 2000.
U.S. Appl. No. 10/026/122, filed Dec. 17, 2002.

* cited by examiner

*Primary Examiner* — Melanie Hand
(74) *Attorney, Agent, or Firm* — Dority & Manning, P.A.

(57) ABSTRACT

An absorbent article, such as a disposable diaper, includes a chassis having a front waist region, a back waist region, and a crotch region extending between the front and back waist regions. An outer cover member and a bodyside liner extend longitudinally between the front and back waist regions. An absorbent body structure is sandwiched between the outer cover member and the bodyside liner. A waistband portion includes at least one elastomeric portion. The waistband portion has a relaxed circumference wherein between about 45% to about 70% of the circumference is defined by the elastomeric portion. The waistband portion has an extended circumference for a target wearer wherein, at the extended circumference, the elastomeric portion is extended between about 10% to about 40% of its relaxed circumferential length.

14 Claims, 3 Drawing Sheets

ABSORBENT ARTICLE WITH AN ELASTIC WAISTBAND HAVING A PREFERRED RATIO OF ELASTIC TO NON-ELASTIC MATERIALS

TECHNICAL FIELD OF THE INVENTION

The present invention relates generally to the field of absorbent articles and garments, such as children's training pants, disposable diapers, incontinence articles, and the like, and more particularly to an improved waistband configuration for use in such articles.

BACKGROUND

Various types of disposable absorbent articles such as disposable diapers, training pants, swim pants, incontinence articles, and the like, utilize a chassis incorporating an absorbent system and an elastomeric waistband. The waistband provides for enhanced fit, comfort to the wearer, and improved product performance.

Much attention has been paid in the art to development of various elastomeric waistband configurations. For example, U.S. Pat. No. 4,205,679 discloses various embodiments of a pull-on pant-like article having gathered elastic waistband portions. U.S. Pat. No. 4,639,949 describes a disposable absorbent garment having an improved elastic waistband with an elastic element joined in a stretched condition to a marginal portion of an exterior panel of the garment with a plurality of spaced bond points. U.S. Pat. No. 4,904,251 describes a disposable diaper having gathered elasticized front and back waistband portions. Tape fasteners are provided on back side flaps for fastening the front and back regions of the article together on a wearer. U.S. Pat. No. 5,676,661 similarly discloses a diaper configuration having elasticized waistband portions and tape members extending from the side margins of the back waist region. The tape members include a fastening strip, such as a hook-type material, that attaches to a corresponding landing pad, material provided on the front waist region to secure the article to a wearer.

With a known commercial disposable diaper (the HUGGIES® brand from Kimberly-Clark Corp. of Neenah, Wis., USA) elasticity is provided to the back waistband portion by elastomeric strips bonded to side edges of the chassis at the waist region. A non-elastic material strip is bonded to the outboard end of the elastomeric strips, and a micro-hook material strip is laminated to this non-elastic material. For securing the diaper on a wearer, the hook material attaches to a piece of non-woven web material adhered to the outer cover at the front waist region. Thus, with this configuration, the chassis has generally non-elastomeric waistband portions, and the desired degree of elasticity is provided around the waist of a wearer by the elastomeric tab strips.

With a typical absorbent article configuration, the circumference of the waist area in a relaxed state is significantly smaller than the waist of an intended wearer in the designed size range of the article. The waist area of the article must thus expand or stretch a significant degree. With many typical absorbent article constructions, the ratio of elastomeric materials to non-elastomeric materials in the waist region when the article is fully retracted is such that the elastomeric materials make up about 5% to about 25% of the entire circumference of the retracted waist area. However, the elastomeric regions are highly retracted and extend (stretch) between about 50% to about 120% of their retracted length on the average target wearer. This results in a relatively high tension being placed on the elastomeric materials in use of the article. With such high tension, stress relaxation of the elastomeric materials becomes a concern. Additionally, waistbands with an excessively high tension of the elastic elements result in an uncomfortable fit, red-marking, and/or difficulty in pulling a pant-like structure up or down.

To ensure that article performance is not degraded over time due to stress relaxation of the elastomeric materials, it is often the case that relatively expensive elastomeric polymers are required that are designed to function with minimal stress relaxation. These elastomeric materials account for a significant portion of the overall cost of the article.

The present invention provides an improved elastic waistband configuration that may help alleviate deficiencies of current configurations.

SUMMARY

Objects and advantages of the invention will be set forth in part in the following description, or may be obvious from the description, or may be learned through practice of the invention.

In general, the present invention relates to a unique elastomeric waistband configuration for use in a variety of absorbent articles, such as disposable diapers, child's training pants, incontinence articles, diaper pants, disposable swim pants, and the like. For purposes of description only, embodiments of an absorbent article according to the invention will be made with reference herein to a disposable diaper. It should be understood that the invention is not limited to disposable diapers.

An absorbent article according to the invention includes a chassis having a front waist region, a back waist region, and a crotch region extending between the front and back waist regions. An outer cover member and a bodyside liner extend longitudinally between the front and back waist regions. An absorbent body structure is sandwiched between the outer cover member and the bodyside liner. The construction of such a chassis, and suitable materials for the chassis, are well known to those skilled in the art.

The article includes a waistband having at least one elastomeric portion. The elastomeric portion may be defined by a generally continuous portion, or may be defined by discrete spaced apart regions. The waistband has a retracted (relaxed) circumference wherein between about 45% to about 70% of the retracted circumference is defined by the elastomeric portion. In an embodiment wherein the article is a disposable diaper, the retracted circumference is defined with reference to an attachment location of the back waist region to the front waist region. With the same attachment location between the front and back waist regions, the waistband has an extended circumference for a target wearer such that, at the extended circumference, the elastomeric portion is extended between about 10% to about 40% of its relaxed circumferential length. For example, with one embodiment, the elastomeric portion is extended between about 17% to about 26% of its relaxed circumferential length.

The elastomeric materials used in the elastomeric portion of the waistband are selected such that the elastomeric portion is stretched less than about one-half of its maximum possible percent elongation. For example, the elastomeric portion may be stretched between about 10% to about 40% of its maximum possible elongation.

In its extended state over a designed target size range of the article, the overall circumference of the waistband portion increases in circumference between about 18% to about 37% of its relaxed circumference. The load loss of the waistband portion in its extended sate may be at least about 25%.

Aspects of the invention will be described below in greater detail with reference to embodiments shown in the figures.

DETAILED DESCRIPTION

Figure 1:
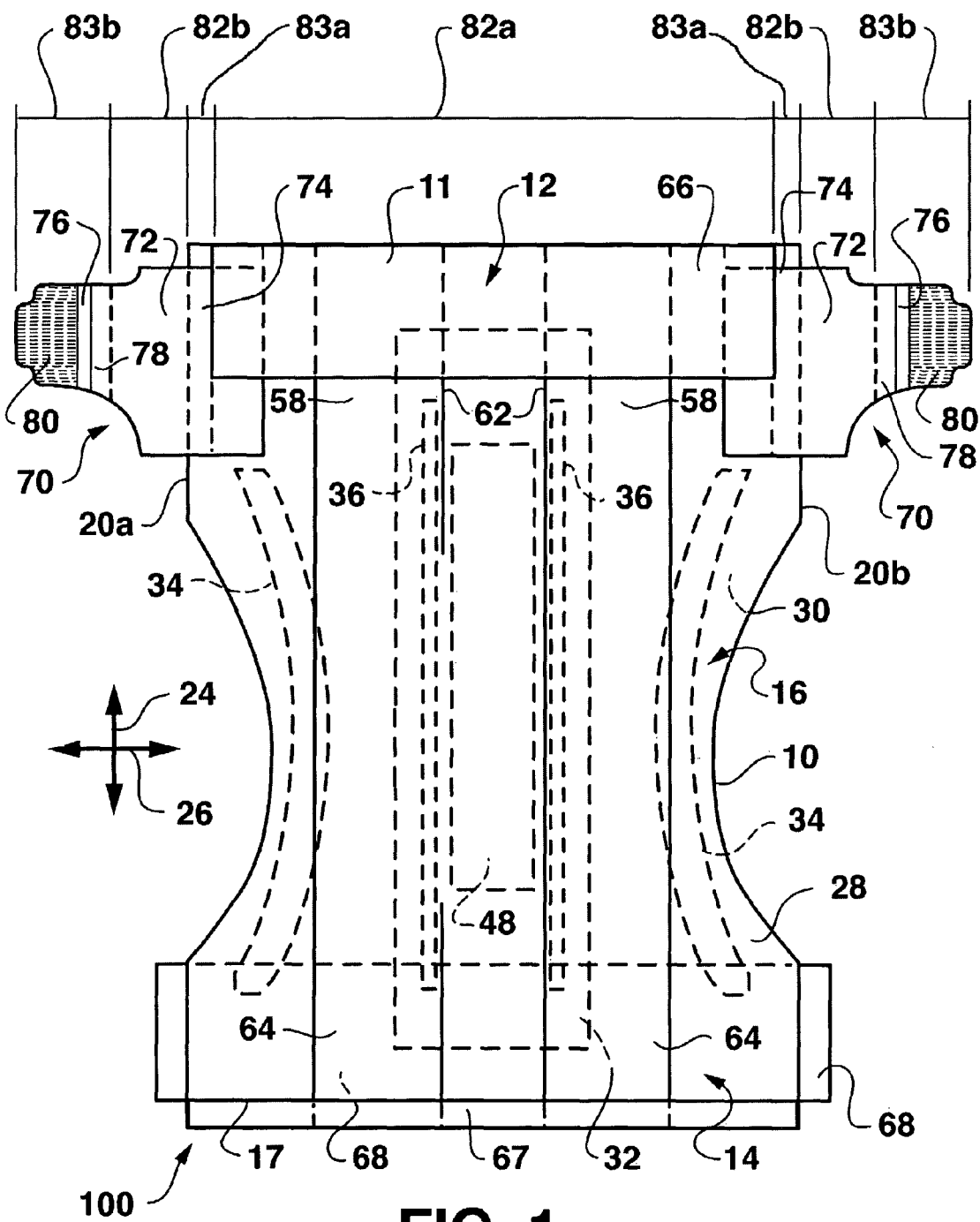
FIG. 1 is a bodyfacing plan view of an embodiment of an article according to the invention shown in an uncontracted condition with all elastic components in a stretched state.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Within the context of the present description, the following terms may have the following meanings:

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Extendable" means that property of a material or composite by virtue of which it stretches or extends in the direction of an applied biasing force normally exerted by a consumer by at least about 25% of its relaxed length without destroying the structure of the material or material fibres. An extendable material may or may not have recovery properties. For example, an elastomeric material is an extendable material having recovery properties. A meltblown web may be extendable, but may not have recovery properties.

"Elastomeric," "elastic," and "elasticized" refer to a material or composite which can be elongated by at least 25% of its relaxed length and which will recover, upon release of the applied force, at least 10% of its elongation. An elastomeric material is an extendable material having recovery properties.

"Neck-bonded" laminate refers to a composite material having an elastic member that is bonded to a non-extensible member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981, 747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415, 4,789,699, 4781,966, 4,657,802, and 4,655,760, which are incorporated herein by reference in their entirety for all purposes.

"Neck stretch-bonded" laminate" refers a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety, by reference thereto for all purposes. Of particular advantage, a necked stretch bonded laminate can be stretchable in both the machine and cross-machine directions.

"Nonwoven web" refers a web that has a structure of individual fibers or threads which are interlaid, but not in an identifiable, repeating manner. Nonwoven webs may be formed, for example, by a variety of processes including melt-blowing, spunbonding, and bonded carded web processes.

"Sheet" refers to a layer which may be either a film or a nonwoven web.

"Member" when used in the singular can refer to a single element or a plurality of elements.

"Tension" refers to a force tending to cause the extension of a body, or to the balancing force within that body resisting the tension. Tension may be expressed in units of grams per unit of width.

Aspects of the invention are explained below by reference to embodiments of a disposable diaper. As mentioned, the invention is not limited to diapers, and as utility for various other absorbent articles, including, training pants, swim pants, incontinence articles, and the like.

FIG. 1 shows a body facing plan view of a representative article 100, in this case a disposable diaper, in its generally flat-out, uncontracted state (i.e., with substantially all elastic induced gathering and contraction removed). The article components are attached or joined together by conventional suitable attachment methods such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the various components.

Figure 2:
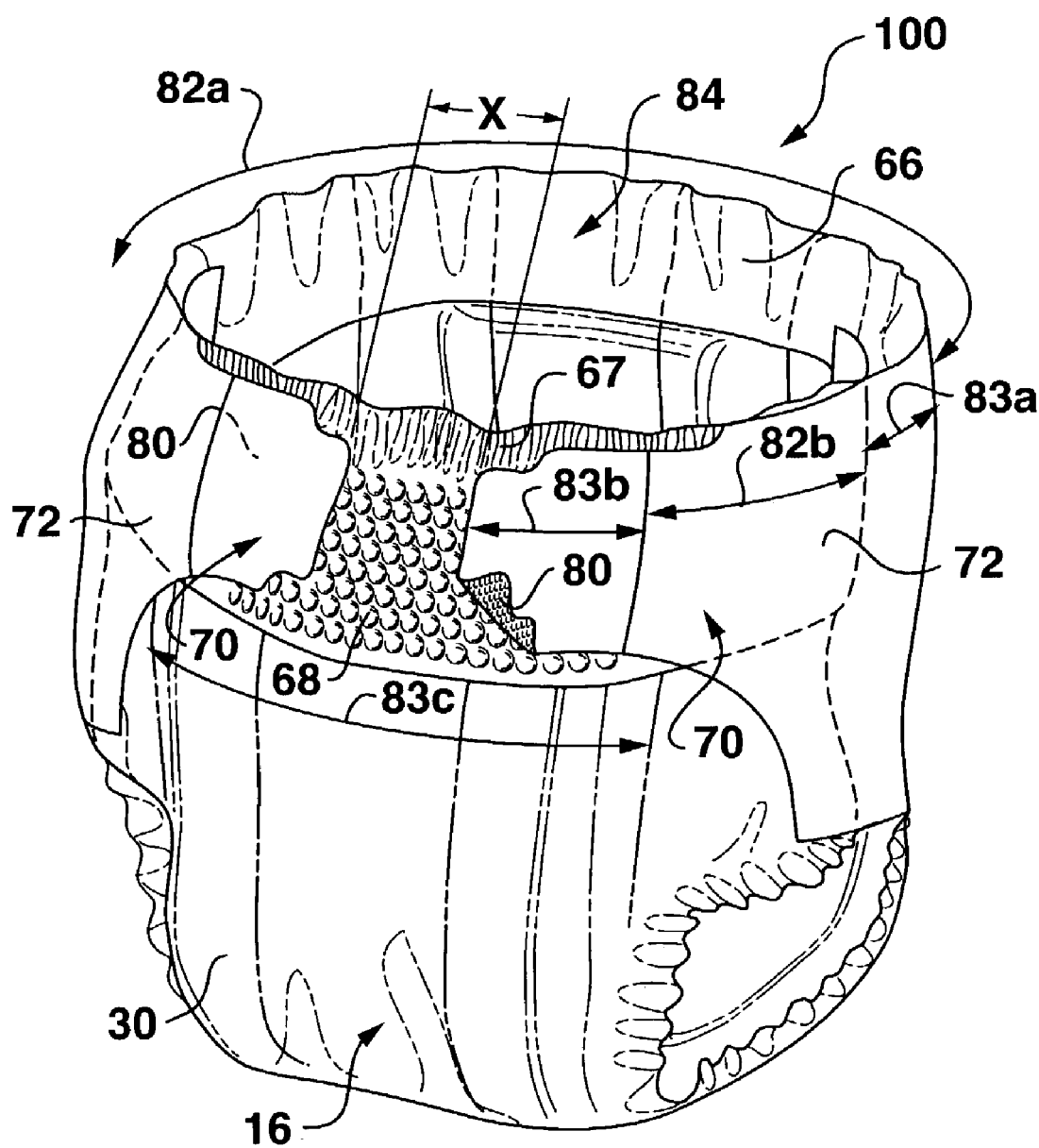
FIG. 2 is a perspective view of the article in FIG. 1 shown in its relaxed or retracted state.

With reference to FIGS. 1 and 2 in general, the representatively shown diaper 100, is illustrated. This diaper 100 is similar in certain aspects to the HUGGIES® brand of disposable diapers from Kimberly-Clark Corporation of Neenah, Wis., USA. The article 100 includes a body or chassis 10 having lateral sides 20a and 20b, a lengthwise, longitudinal direction 24, a lateral direction 26, a front waist region 14, a back waist region 12, and an intermediate crotch region 16 interconnecting the front and back waist regions. The waist regions 12 and 14 comprise those portions of the article 100 which when worn, wholly or partially cover or encircle the waist or mid-lower torso of the wearer. The front 14 and back 12 waist regions have front and back waistband portions 17, 11. The intermediate crotch region 16 lies between and interconnects the waist regions 14 and 12, and comprises that portion of the article 100 which, when worn, is positioned between the legs of the wearer and covers the lower torso of the wearer. Thus, the intermediate crotch region 16 is an area where repeated fluid surges typically occur in the training pant or other disposable absorbent article.

The diaper 100 will typically include a porous, liquid permeable bodyside liner 28 overlying an absorbent body structure 32, and a substantially liquid impermeable outer cover member 30. The absorbent body structure 32 is positioned and attached between the outer cover member 30 and bodyside liner 28. In certain embodiments, a surge layer 48 may be optionally located adjacent the absorbent structure and attached, for example, by way of an adhesive.

The outer cover member 30 and bodyside liner 28 may be separate sheets joined at the respective lateral sides 20a and 20b. Leg elastics 34 may be incorporated along the lateral side margins of the chassis 10 outboard of the absorbent body structure 32 and are configured to draw and hold the chassis 10 against the legs of the wearer. The elastic members 34 are secured to the chassis 10 in an elastically contracted state so that in a normal under-strain condition, the elastic members 34 effectively contract against the chassis. The use of elastic leg members in absorbent articles such as disposable diapers and training pants is widely known and understood in the art.

Various materials are available and known in the art for use as the outer cover member 30. Constructions of the outer cover member 30 may comprise a woven or non-woven fibrous web layer which has been totally or partially constructed or treated to impart the desired levels of liquid impermeability to selected regions that are adjacent or proximate the absorbent body. Alternatively, a separate liquid impermeable material could be associated with the absorbent body structure 32. The outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover member 30 typically provides the outermost layer of the article, optionally the article may include a separate outer cover component member which is additional to the outer cover member.

The outer cover member 30 may be formed substantially from an elastomeric material. Alternately, the outer cover member may be formed from a non-elastomeric and non-extendable material, or a non-elastomeric and extensible material. The outer cover member 30 may, for example, be composed of a single layer, multiple layers, laminates, spunbond fabrics, films, meltblown fabrics, elastic netting, microporous web, bonded carded webs or foams comprised of elastomeric or polymeric materials.

The bodyside liner 28 may be formed from any one or combination of suitable materials known in the art. Various woven and nonwoven fabrics can be used as the liner 28. For example, the material may include a meltblown web, a spunbonded web, or a bonded-carded-web composed of synthetic continuous or discrete polymer fibers and/or natural fibers, a pattern bonded spunbonded web, airlaid web, or bonded carded web, as well as combinations thereof. The various fabrics can be composed of natural fibers, synthetic fibers or combinations thereof. In particular aspects, the material may be comprised of polymer fibers, networks, laminates, liquid permeable films, cellulosic fibers, rayon, water swellable gels, as well as combinations thereof. Suitable polymers can include polypropylene, polyethylene, polyester, and bicomponent materials composed of these polyolefins. The liner may be elastomeric or extensible or both.

The liner 28 may be composed of a substantially hydrophobic material, and the hydrophobic material may optionally be treated with a surfactant or otherwise processed to impart a desired level of wettability and hydrophilicity. In a particular embodiment of the invention, the material can be a nonwoven, spunbond polypropylene fabric. The fabric can be surface treated with an operative amount of surfactant, such as about 0.6% AHCOVEL Base N62 surfactant, available from ICI Americas, a business having offices located in Wilmington, Del. The surfactant can be applied by any conventional means, such as spraying, dipping, printing, brush coating or the like. The fibers forming the nonwoven material may be mono-component, bi-component, or multi-component fibers, and combinations thereof.

The liner 28 may include blends or laminates of fibers, scrim, webs, and films with perforations, apertures, creping, heat activation, embossing, micro-straining, chemical treatment, or the like, as well as combinations thereof.

The article 100 may incorporate separate containment flaps 58 attached to the chassis 10 at the waistband portions 11, 17 and along a longitudinal side thereof outboard of the absorbent structure 32. The flaps 58 may contain elastic members 36 along at least a portion of their free laterally inward side 62. The flaps 58 have a laterally outboard side 64 attached to the liner 28. The construction of such containment flaps 58 is well known and need not be described in detail. Suitable constructions and arrangements for the containment flaps 58 are described, for example, in U.S. Pat. No. 4,704,116, which is incorporated herein by reference for all purposes.

The absorbent body structure 32 can be any structure or combination of components that are generally compressible, conformable, non-irritating to a wearer's skin, and capable of absorbing and retaining liquids and certain body wastes. The structure 32 may be extensible or elastomeric. For example, the structure 32 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., USA, and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable wrap that aids in maintaining the integrity and shape of the absorbent structure 32.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent body structure 32 may include an elastomeric coform absorbent web material, for example as described in U.S. Pat. Nos. 4,663,220 and 4,741,949. In particular aspects, the elastomeric coform material can have an overall coform basis weight which is at least a minimum of about 50 g/m$^2$. The coform basis weight can alternatively be at least about 100 g/m$^2$ and can optionally be at least about 200 g/m$^2$ to provide improved performance. In addition, the coform basis weight can be not more than about 1200 g/m$^2$. Alternatively, the coform basis weight can be not more than about 900 g/m$^2$, and optionally, can be not more than about 800 g/m$^2$ to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389 B1, incorporated herein by reference for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 200-900 grams of 0.9 wt % saline, and can typically be about 500 g of saline. For adult care products, the total absorbency can be within the range of about 400-2000 grams of saline, and can typically be about 1300 g of saline. For feminine care products, the total absorbency can be within the range of about 7-50 grams of menstrual fluid, and can typically be within the range of about 30-40 g of menstrual fluid.

As described, the absorbent body structure 32 may also include a surge management layer 48 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 28. Alternatively, the surge layer may be located on the body facing surface of the bodyside liner 28. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference in their entirety for all purposes.

Referring to FIG. 2, the article 100 is depicted in its attached state wherein the back waist portion 11 is attached to the front waist portion 17 to define a relaxed waist circumference 84. The waist circumference 84 includes at least one elastomeric portion. As discussed in greater detail below, the elastomeric portion may be defined by a continuous circumferential strip or region of elastomeric material, or circumferentially spaced apart discrete regions of elastomeric material. The "continuous" circumferential strip may include overlapping portions of different elastomeric materials.

Referring to FIG. 1, the article 100 is illustrated in a flat-out state. The back waist region 11 incorporates a transversely extending strip of elastomeric material 66 extending across a substantial portion of the waist region. The elastomeric material 66 may be any one of a number of suitable elastomeric materials. For example, the material 66 may be an elastomeric nonwoven laminate webs including a nonwoven material joined to one or more gatherable nonwoven webs, films, or foams. Stretch bonded laminates (SBL), neck bonded laminates (NBL), and necked stretch bonded Laminates (NSBL) are examples of elastomeric composites. Nonwoven fabrics are any web of material which has been formed without the use of textile weaving processes which produce a structure of individual fibers which are interwoven in an identifiable repeating manner. Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films or filaments, foams, or meltblown fabrics composed of polyethylene, polypropylene, or polyolefin copolymers, as well as combinations thereof. The outer cover 30 may include materials that have elastomeric or extensible properties obtained through a mechanical process, printing process, heating process, or chemical treatment. For example such materials may be apertured, creped, neck-stretched, heat activated, embossed, and micro-strained; and may be in the form of films, webs, and laminates.

The elastomeric material 66 is bonded to the chassis 10 across the cross-dimensional width of the back waist region 11. Referring to the grid line above the article 100 in FIG. 1, the portion of the back waist region 11 defined as 82a is elastic due to incorporation of the elastomeric material 66. The laterally extending regions 83a corresponding to the bond areas 74 are generally non-elastic.

The article 100 includes attachment tabs 70 bonded to the chassis along the bond areas 74 extending laterally from the chassis edge to the laterally outboard edge of the elastomeric material 66. The attachment tabs 70 are defined by a suitable elastomeric material 72. Thus, referring to the grid line in FIG. 1, the regions designated 82b are also elastic regions and contribute to the overall elasticity of the waist circumference.

Still referring to the attachment tabs 70, pieces of non-elastomeric material 76, such as a non-woven material, are attached to the laterally outboard edges of the elastomeric material 72 at the longitudinally extending bond areas 78. A micro-hook material 80 is attached to the body facing side of the non-elastomeric material 76. Referring to the grid line in FIG. 1, the laterally extending areas 83b defined by the non-elastomeric materials 76 and microhook material 80 are non-elastic regions, even though there may be some overlap of elastic and non-elastic materials in these regions. For the region to be elastomeric, it must contain elastic material that is free to extend. In an alternate embodiment, the materials 76 and 80 may be elastic and the areas 83b would thus also be elastomeric regions.

With reference to the grid line in FIG. 1, it can be seen that the central portion 82a and portions 82b defined by the tabs 70 are elastomeric regions and contribute to the stretchability of the waist. The regions 83a and 83b are non-elastomeric materials and do not stretch in the lateral direction.

The front waist region 17 includes a laterally extending strip or piece of nonwoven material 68 attached to the outer cover material 30. This material defines an attachment or "landing" region for attachment of the micro-hook material 80, as is generally understood in the art. In the illustrated embodiment, the material 68 is a nonwoven material having regions of raised loops containing nonwoven filaments with an embossed or bonded pattern defined between the loops. The micro-hook material 80 securely attaches to the raised portions of the material. The material 68 is non-elastomeric and, thus, the front waist region 17 does not expand in the lateral direction. The edge portion 67 of the front waist region may include strands of elastomeric material. However, this edge 67 serves the purpose to generally seal the edge of the article against the wearer's abdomen, and does not add to the stretchability of the waist region. The front of the article does not contribute to the elastic portion of the illustrated embodiment. However, elastic nonwoven material 68 could be employed, but the extension would not be included in the calculations for circumference and/or load loss.

Referring to FIG. 2, the article 100 is shown in its attached state with the attachment tabs 70 attached to the band of non-woven material 68 extending across the front waist region of the article. The article 100 is designed so that a lateral distance X is defined between the ends of the tabs 70 when the article 100 is properly positioned on a wearer. This distance X is typically about 50 mm (but may range between 10 to about 150 mm). For disposable diapers, the various sizes of diapers are designed for a target size range of wearer such that the distance X between the tabs is maintained relatively constant, for example at or about 50 mm. Thus, it should be understood that the circumference 84 of the article 100 in its relaxed condition as shown in FIG. 2 is defined by the length of the grid line illustrated in FIG. 1, plus the distance X between the ends of the attachment tabs 70.

In accordance with the invention, about 45% to about 70% of the relaxed circumference 84 is defined by the total elastomeric portion of the waistband. In the illustrated embodiment, the total elastomeric portion is defined by the elastomeric regions 82a and 82b.

Figure 3:
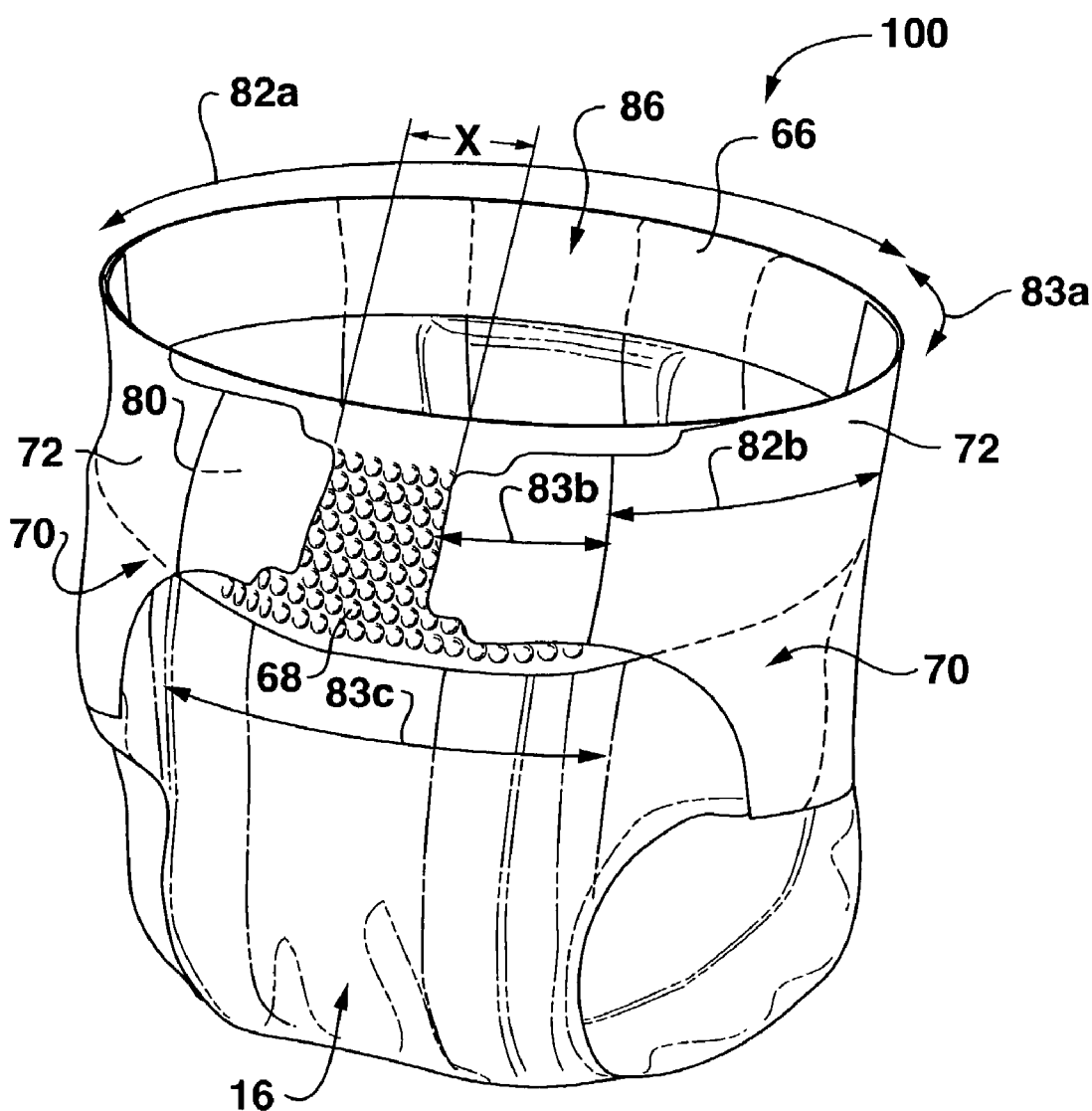
FIG. 3 is a perspective view of the article in FIG. 2 shown in its stretched condition as it would be worn on a user.

FIG. 3 illustrates the diaper in its expanded state as it would be worn by a wearer. The article 100 defines an extended circumference 86. The circumference 86 is defined by the non-elastomeric region 83c extending across the front waist region (includes the regions 83b and material 68 spanning the lateral space X), the elastomeric regions 82b defined by a portion of the attachment tabs 70, the non-elastomeric regions 83a defined by the bond areas 74, and the elastomeric region 82a. At this extended circumference 86, the elastomeric portion of the waistband (regions 82a and 82b) are extended or stretched in the lateral direction between about 10% to about 40% of their relaxed circumferential length shown in FIG. 2. In one particular embodiment, the total elastomeric portion is extended between about 17% to about 26% of its relaxed circumferential length.

The article 100 is designed such that, at the extended circumference 86, the waistband portion is increased in circumference between about 18% to about 37% of its relaxed circumference 84 illustrated in FIG. 2.

At the extended circumference of the article 100 as illustrated in FIG. 3, load loss of the waistband portion may be at least about 25 percent. "Load loss" of the system is defined as the loss in force over time at a constant circumference of the article (or under a constant strain). As explained, the elastomeric portion of the waistband may include discrete regions of the elastomeric material, as in the illustrated embodiment. Here, the load loss of the waistband system is the loss in all of the elastomeric materials at the elongation strain applied to the entire waistband.

As described, at the extended circumference 86, the total elastomeric portion of the waistband is stretched between about 10% to about 40% of its relaxed circumferential length. Desirably, the elastomeric materials are stretched significantly less than their maximum possible percent elongation, for example less than about one half of their possible percent elongation. In a particular embodiment, the elastomeric materials are stretched between about 10 percent to about 40 percent of their maximum possible elongation.

The following comparative data is provided by way of further explanation of the invention:

Three product samples were tested: (1) an Ultratrim® diaper from Kimberly-Clark Corp.; (2) a Custom Fit diaper from Proctor & Gamble Corp.; and (3) a diaper configured in accordance with the present invention. With reference to FIGS. 1 and 2, the following applies:

extended circumference 86 on average child=480 mm
relaxed circumference 84 as stated
percent increase in circumference=(480 mm−relaxed circumference 84)/relaxed circumference 84
elastomeric portion=82a+82b
percentage of relaxed circumference defined by elastomeric portion=(82a+82b)/relaxed circumference
percent extension of elastomeric portion at extended circumference=(480 mm−relaxed circumference 84−tab spacing of 50 mm)/elastomeric portion (82a+82b)

TABLE

|  | ULTRATRIM ® | CUSTOM FIT | APPLICATION SAMPLE |
|---|---|---|---|
| Extended Circumference 86 | 480 mm | 480 mm | 480 mm |
| Relaxed Circumference 84 | 390 mm | 370 mm | 370 mm |
| % Increase in Circumference | 23% | 30% | 30% |
| Elasto- | 0 | 0 | 170 |

TABLE-continued

|  | ULTRATRIM ® | CUSTOM FIT | APPLICATION SAMPLE |
|---|---|---|---|
| meric Portion 82a |  |  |  |
| Elastomeric Portion 82b | 34 | 100 | 80 |
| Total Elastomeric Portion (82a + 82b) | 34 | 100 | 250 |
| % Extension of Elastomeric Portions at Extended Circumference | 118% | 60% | 24% |
| % of Relaxed Circumference Defined by Elastomeric Portions | 9% | 27% | 67.5% |

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. An absorbent article, comprising:
    a. a chassis, wherein said chassis includes a front waist region, a back waist region, and an intermediate region connecting said front and back waist regions and wherein said front and back waist regions define a circumference when connected;
    b. a substantially liquid permeable bodyside liner and a substantially liquid impermeable outer cover extending longitudinally between said front and back waist regions;
    c. an absorbent body between said liner and said outer cover;
    d. an elastomeric region in at least one of said front and back waist regions, wherein said elastomeric region extends across approximately 45% to 70% of said circumference;
    e. wherein said elastomeric region experiences at least approximately 25% load loss upon stretching to increase said circumference from approximately 10% to no more than 40%.

2. The absorbent article as in claim 1, wherein said elastomeric region includes at least two spaced apart regions of elastomeric material.

3. The absorbent article as in claim 1, wherein said front waist region is non-elastomeric.

4. The absorbent article as in claim 1, wherein said elastomeric region may be extended approximately 17% to 26% of said circumference.

5. The absorbent article as in claim 1, wherein said elastomeric region comprises a continuous, unitary portion of said back waist region.

6. The absorbent article as in claim 5, wherein said continuous, unitary portion of said back waist region comprises elastomeric attachment tabs.

7. The absorbent article as in claim 6, wherein said attachment tabs include non-elastomeric material at a distal end.

8. The absorbent article as in claim 1, wherein said absorbent article comprises a diaper.

9. The absorbent article as in claim 1, wherein said absorbent article is a child's training pant.

10. The absorbent article as in claim 1, wherein said absorbent article is an adult incontinence article.

11. An absorbent article, comprising:
    a chassis, wherein said chassis includes a front waist region, a back waist region, and an intermediate region connecting said front and back waist regions and wherein said front and back waist regions define a circumference when connected;
    a substantially liquid permeable bodyside liner and a substantially liquid impermeable outer cover extending longitudinally between said front and back waist regions;
    an absorbent body between said liner and said outer cover;
    a continuous, unitary elastomeric region in said back waist region, wherein said elastomeric region extends across approximately 45% to 70% of said circumference;
    wherein said elastomeric region experiences at least approximately 25% load loss upon stretching to increase said circumference from approximately 10% to no more than 40%.

12. The absorbent article as in claim 11, wherein said front waist region is non-elastomeric.

13. The absorbent article as in claim 11, wherein said continuous, unitary elastomeric region comprises elastomeric attachment tabs.

14. The absorbent article as in claim 13, wherein said attachment tabs include non-elastomeric material at a distal end.

* * * * *